United States Patent [19]

Dorawala et al.

[11] 4,310,715

[45] Jan. 12, 1982

[54] STEAM DEALKYLATION PROCESS

[75] Inventors: Tansukhlal G. Dorawala, Wappingers Falls; Russell R. Reinhard, Hopewell Junction; Edwin R. Kerr, Wappingers Falls, all of N.Y.

[73] Assignee: Texaco, Inc., White Plains, N.Y.

[21] Appl. No.: 628,287

[22] Filed: Nov. 3, 1975

[51] Int. Cl.$^3$ .......................... B01J 23/64; C07C 4/12
[52] U.S. Cl. .................... 585/487; 252/420; 252/470
[58] Field of Search .............. 266/672; 252/470; 585/487

[56] References Cited

U.S. PATENT DOCUMENTS

| | | | |
|---|---|---|---|
| 2,960,545 | 11/1960 | Seubold | 260/672 |
| 3,433,732 | 3/1969 | Leaman | 252/420 X |
| 3,595,932 | 7/1971 | Nossonovich et al. | 260/672 |
| 3,609,079 | 9/1971 | Koppe | 252/420 X |
| 3,681,258 | 8/1972 | Pitzer | 252/420 X |
| 3,751,503 | 8/1973 | Sampson et al. | 260/672 |
| 3,775,504 | 11/1973 | Sampson et al. | 260/672 |
| 3,812,196 | 5/1974 | Uchiyama et al. | 260/672 |
| 3,829,519 | 8/1974 | Sampson et al. | 260/672 |
| 3,848,014 | 11/1974 | Uchiyama et al. | 260/672 |
| 3,884,987 | 5/1975 | Uchiyama et al. | 260/672 |
| 3,903,186 | 9/1975 | Ohsumi et al. | 260/672 |
| 3,907,916 | 9/1975 | Sonderquist et al. | 252/420 X |

*Primary Examiner*—Robert V. Hines
*Attorney, Agent, or Firm*—Carl G. Ries; Robert A. Kulason; Carl G. Seutter

[57] ABSTRACT

Alkylaromatic hydrocarbons are dealkylated in a short cycle process characterized by a reaction period of 30–180 seconds followed by a regeneration period of 90–540 seconds—thus permitting attainment of improved conversion and yield of desired product.

19 Claims, No Drawings

STEAM DEALKYLATION PROCESS

FIELD OF THE INVENTION

This invention relates to the conversion of hydrocarbons. More particularly, it relates to the dealkylation of alkylaromatic hydrocarbons such as toluene.

BACKGROUND OF THE INVENTION

As is well known to those skilled in the art, steam dealkylation has commonly been carried out by passing an alkylaromatic hydrocarbon, typically toluene, together with steam through a furnace at 650° F.–950° F. to yield a product containing principally benzene. Steam dealkylation is carried out in the presence of catalysts; and typical catalyst compositions may include zeolites or amorphous inorganic oxides such as silica, alumina, silica-alumina magnexia, zirconia, etc. commonly bearing metal oxides. It is found that typical prior art processes are less than fully satisfactory because of low yields of product, degradation of catalyst, poor product selectivity etc.

It is an object of this invention to provide a steam dealkylation process particularly characterized by high conversion and high yield. Other objects will be apparent to those skilled in the art.

STATEMENT OF THE INVENTION

In accordance with certain of its aspects, the novel process of this invention for dealkylating an alkylaromatic hydrocarbon charge may comprise passing a mixture of steam and charge alkylaromatic hydrocarbon into contact with a steam dealkylation catalyst at steam dealkylating conditions for 30–180 seconds during which time the activity of the steam dealkylation catalyst, as measured by the mole percent conversion of charge alkylaromatic hydrocarbon to product dealkylated alkylaromatic hydrocarbon, decreases during a reaction period;

interrupting said reaction period when the activity of said catalyst has decreased;

contacting said catalyst of decreased activity with steam during a regeneration period at regeneration conditions for 90–540 seconds, as the activity of said catalyst increases, thereby forming regenerated catalyst; and recovering product dealkylated alkylaromatic hydrocarbon.

DESCRIPTION OF THE INVENTION

In accordance with certain of its aspects, the charge alkylaromatic hydrocarbon which may be treated by the process of this invention may be a stream typically having a boiling point of 176° F.–1292° F. (80° C.–700° C.). The stream may contain alkylaromatic hydrocarbons, either pure or in admixture, in varying quantities. This charge stream may typically contain toluenes, xylenes, ethyl benzenes, propyl benzenes etc. The preferred charge hydrocarbon contains a toluene; and in the preferred embodiment, it may be substantially entirely toluene se. In another embodiment of the invention, the charge stream may contain hydrocarbons having 9–11 carbon atoms, typified by trimethylbenzene; indane; methylethyl benzenes; methyl naphthalenes; etc.

Typical charge streams which may be treated by the process of this invention may include aromatic extracts or reformate streams containing alkylaromatic hydrocarbons. Illustrative of such charge streams may be a reformate commonly containing the following components (% by volume);

TABLE

| Component | Broad | Typical |
|---|---|---|
| Paraffins | 30–45 | 40 |
| Olefins | 0–2 | 1 |
| Naphthenes | 1–5 | 3 |
| Aromatics | 45–65 | 56 |

Of the aromatic content of the reformate, 80%–100%, typically 90% may be present as alkylaromatic hydrocarbons.

This reformate may have a (RON Clear) octane number of 90, an IBP of 115° F., an EBP of 410° F., and an API gravity of 47.7.

Particularly desirable results may be achieved by use, as the hydrocarbon charge, of compositions containing substantial proportions of toluene.

The steam dealkylation catalysts which may be used in practice of the process of this invention may be supported catalysts or unsupported catalysts. Typical of the unsupported catalysts may be those containing oxides of a Group VIII metal and of a Group VI B metal. The Group VIII metal may include iron Fe, cobalt Co, nickel Ni, ruthenium Ru, rhodium Rh, palladium Pd, osmium Os, iridium Ir, and platinum Pt. Preferably the Group VIII metal may be nickel or cobalt; and in the most preferred embodiment, it is nickel.

The Group VI B metal may be chromium Cr, molybdenum Mo, or tungsten W; and in the preferred embodiment, it is chromium Cr.

A preferred unsupported catalyst may contain nickel and chromium and may be characterized by the formula $$xNiO:yCr_2O_3$$

wherein x is 6–96, preferably 19–83, say 56 and y is 4–94, preferably 17–81, say 44. Typical of such catalysts is that available as 50 Ni–50 $Cr_2O_3$ which in fact corresponds to the formula 56 NiO: 44 $Cr_2O_3$.

A preferred supported catalyst which may be employed in practice of the process of this invention may comprise a catalyst support containing oxides of a Group VIII metal and of a Group I A metal plus preferably oxides of a metal of Group VI B.

The Group I A metal, an alkali metal, may be lithium Li, sodium Na, potassium K, rubidium Rb, or caesium Cs. In the preferred embodiment, it is potassium K.

The catalyst support may be active or inactive or inert. Typically the support may be a clay, a silica, a metal oxide, a zeolite, etc. The preferred porous materials may include alumina, silica, silica-alumina, silica-magnesia, silica-titania, silica-beryllia, silica-zirconia, silica-alumina-magnesia, etc. The preferred support is an inert support such as alumina, preferably gamma-alumina.

In typical practice of the process of this invention, the supported catalyst composition may contain the following components in the indicated parts by weight (expressed as oxide):

TABLE

| Component | Broad | Preferred | Typical |
|---|---|---|---|
| Group VIII Fe—Co—Ni or | 5–40 | 6–20 | 15 |

TABLE-continued

| Component | Broad | Preferred | Typical |
| --- | --- | --- | --- |
| Ru—Rh—Pd Os—Ir—Pt | 0.5–10 | 0.5–5 | 1 |
| Group VI B | 0–40 | 10–38 | 15 |
| Group I A | 0.01–5 | 1–4 | 2 |
| Support | 15–99.5 | 38–84 | 68 |

The preferred catalyst may be that containing nickel-chromium-potassium-aluminum; and the catalyst composition may contain the following (expressed as oxide):

TABLE

| Component | Broad | Preferred | Typical |
| --- | --- | --- | --- |
| Ni | 5–40 | 6–20 | 15 |
| Cr | 0–40 | 10–38 | 15 |
| K | 0.01–5 | 1–4 | 2 |
| Al | 15–99.5 | 38–84 | 68 |

In terms of molar proportions, the catalyst may be represented by the formula $$a(VIII)_{2/n}O:b(VI)_{2/m}O:c(I)_2O$$

wherein (VIII) represents a metal of Group VIII of the Periodic Table having a valence n, (VI) represents a metal of Group VI B of the Periodic Table having a valence m, (I) represents a metal of Group I A of the Periodic Table. a may be 0.002–0.75, preferably 0.002–0.38, say 0.20; b may be 0–0.78, preferably 0.13–0.75, say 0.29; and c may be 0.00003–0.17, preferably 0.003–0.13, say 0.02.

In one preferred embodiment, the catalyst may be represented by the formula $$aNiO:bCr_{2/3}O:cK_2O$$

wherein a is 0.08–0.54, preferably 0.08–0.27, say 0.20; b is 0–0.78, preferably 0.21–0.75, say 0.29; and c is 0.01–0.05 preferably 0.01–0.04, say 0.02.

When the support is alumina, as in the preferred embodiment, the catalyst composition may be represented by the formula $$aNiO:bCr_{2/3}O:cK_2O:dAl_2O_3$$

wherein a, b and c are as supra and d is 0.15–0.95, preferably 0.38–0.84, say 0.68.

The supported catalyst may be prepared by immersing a catalyst support in a solution containing the metal ions. The support, typically a gamma-alumina extrudate of 1.5 mm diameter and 10 mm length may first be steam sintered at 900°–1400° F., say 1110° F. for 5–25 hours, say 12 hours. During sintering, there may be passed through the bed air at VHSV of 40–600, say 230 together with steam at VHSV of 0.05–0.1, say 0.06. (All VHSV are measured at standard composition and pressure unless otherwise stated) The steamed alumina is then calcined for 1–5, say 2 hours at 900° F.–1200° F., say 1000° F. The initial surface of the alumina, typically 200–400, say 231 meter$^2$/gram may be decreased to 70%–95%, say about 90% to a value of 140–380, say 192 meter$^2$/gram.

The support (typically 242 parts), preferably as so treated, is cooled to 32° F.–80° F., say about 32° F. and wetted with 200–2525 parts, say 890 parts of solution prepared by dissolving soluble decomposable salts of metals of Group VI B and Group I A in aqueous solution. Preferably 5–1000 parts more preferably 200–1000, say 792 parts of salt of Group VI B metal, typically chromium nitrate nonahydrate Cr $(NO_3)_3.9H_2O$ and 5–25 parts, preferably 10–23 say 17.2 parts of salt of Group I A metal, typically potassium nitrate are dissolved in 10–1500 parts, say 80 parts of water to yield total solution in amount of 20–2525 parts, say 890 parts. (Although nitrates of the metals are preferably employed, acetates, formates, citrates, or other soluble, decomposable salts may be used.

The solution is poured over the support and is stirred intermittently for 0.5–10 hours, say 1 hour; and the solution (50–2400 parts, typically 731 parts) may then be decanted. The impregnated support is dried at 212° F.–400° F., say 300° F., then heated to decomposition temperature of typically 650° F.–1000° F., say 700° F., and calcined for 1–10 hours, say 2 hours at 700° F.–1400° F., say 1000° F. This procedure is preferably repeated 2–4, preferably 2 times more until all the metal salt solution is absorbed by the support. The final pre-catalyst so prepared in amount of 242–1500 parts, say 383 parts may be characterized by the formula $$b(VI)_{2/m}O.c(I)_2O.dAl_2O_3$$

wherein (VI) represents a metal having valence m of Group VI B of the Periodic Table, (I) represents a metal of Group I A of the Periodic Table, b is 0–0.78, preferably .0.13–0.75, say 0.28, c is 0.00003–0.17, preferably 0.003–0.13, say 0.02, and d is 0.15–0.95, preferably 0.38–0.84, say 0.68. (Supports other than or in addition to $Al_2O_3$ may be present).

In one preferred embodiment, the composition of the pre-catalyst may be $$bCr_{2/3}O:cK_2O:d\ Al_2O_3$$

where b is 0.25, c is 0.02, d is 0.59.

292–1500 parts, say 383 parts of pre-catalyst may be cooled to 32° F.–80° F., say 32° F. and impregnated with decomposable soluble salt of a Group VIII metal. Preferably the solution may contain 50–700 parts, say 267 parts of $Ni(NO_3)_2.6H_2O$ in 50–1400 parts, say 263 parts of water. After 0.5–10 hours, say 1 hour of intermittent stirring, the excess non-absorbed solution is decanted and the solids dried for 2–18 hours, say 16 hours at 212° F.–400° F., say 300° F. The dried solid is reimpregnated with the remaining salt solution for 0.5–10 hours, say 1 hour and dried again for 2–18 hours, say 16 hours at 212° F.–400° F., say 300° F. Further treatment includes heating for 0.5–24 hours, say 1 hour, at 650° F.–1000° F., say 700° F. in a flowing stream of air to decompose the decomposable salts, typically nitrates, and then calcining for 1–10 hours, say 2 hours at 600° F.–1000° F., say 700° F. to yield 260–1850 parts, say 462 parts having a density of 0.7–1.5, say 1.11.

The product catalyst so prepared may be characterized by the formula $$a(VIII)_{2/n}O:b(VI)_{2/m}O:c(I)_2O:d(Supp)$$

wherein all the symbols are as noted supra except that a is 0.002–0.75, preferably 0.002–0.38, say 0.20, (VIII) represents a metal, having a valence n, of Group VIII of the Periodic Table, preferably nickel, and (Supp) represents the catalyst support, preferably $Al_2O_3$.

Preferred catalyst compositions may have the formula:

$$0.23NiO:0.02K_2O:0.79Al_2O_3$$

$$0.2NiO:0.1Cr_{2/3}O:0.02K_2O:0.68Al_2O_3$$

$$0.17NiO:0.25Cr_{2/3}O:0.02K_2O:0.48Al_2O_3$$

$$0.20CoO:0.20Cr_{2/3}O:0.02Na_2O_3:0.34SiO_2$$

Expressed on a weight basis, the catalyst may have the composition set forth in the following Table:

TABLE

| Component | Broad | Preferred | Typical |
|---|---|---|---|
| Group VIII Fe—Co—Ni Ru—Rh—Pd | 6–40 | 6–20 | 15 |
| Os—Ir—Pt | 0.5–10 | 0.5–5 | 1 |
| Group VI B | 0–40 | 10–38 | 15 |
| Group I A | 0.01–5 | 1–4 | 2 |
| Support | 15–99.5 | 38–84 | 68 |

A preferred composition may contain 17.7% NiO 13.2% $Cr_2O_3$, 1.9% $K_2O$, and 61.6% $Al_2O_3$. Another preferred composition may contain 11.9% NiO, 30.4% $Cr_2O_3$, 1.4% $K_2O$, and 48.2% $Al_2O_3$. Another preferred composition may contain 15.5% NiO, 1.8% $K_2O$, and 74.1% $Al_2O_3$—percentages in this paragraph being on a weight basis.

The catalyst composition may be in the form of pellets, cylinders, or randomly shaped particles; a typical catalyst composition may be in the form of cylinders, of diameter 1–15 mm, say 1.5 mm and height 1–15 mm, say 8–10 mm.

The catalyst may be activated prior to use (eg in steam dealkylation). Preferably activation may be carried out by the process which comprises (a) maintaining the unactivated catalyst in a hydrogen atmosphere at 950° F.–1400° F. for 10–30 hours thereby forming a hydrogen-treated catalyst;

(b) maintaining the hydrogen-treated catalyst in a steam-hydrogen atmosphere at 950° F.–1400° F. for 2–10 hours thereby forming a steamed hydrogen-treated catalyst; and (c) preferably cooling the steamed hydrogen-treated catalyst to 650° F.–900° F. in a steam or steam-hydrogen atmosphere thereby forming an activated catalyst.

Activation of the steam dealkylation catalyst may preferably be carried out after the catalyst is in place in the reaction vessel. The vessel may be filled with catalyst composition to a bed bulk density of 50–80 pcf, say 70 pcf. In the first portion of the activation operation, the catalyst composition is heated to 750° F.–1400° F., preferably 900° F.–1100° F., say 1100° F. in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components including oxygen.

The gas may contain (in addition to hydrogen) helium or more preferably light paraffins such as methane, ethane, propane, etc. Hydrogen may be present typically in amount of 30 mole %–100 mole %, preferably 80 mole %–100 mole %, say 100 mole %; i.e. the preferred embodiment may be that in which the gas consists essentially of hydrogen.

Preferably the catalyst composition may be maintained for 10–30 hours, typically 14–16 hours, say 15 hours in a stream of flowing hydrogen typically flowing at a space velocity VHSV (STP) greater than about 3, more preferably greater than 100, say 100–500, typically 300.

When activation is carried out at atmospheric pressure, as in the preferred embodiment, the partial pressure of hydrogen may be at least about 9 psia (400 mm Hg), preferably 12–15 psia, say 15 psia (760 mm Hg).

In the preferred second portion of the activation cycle, the hydrogen-treated catalyst may be maintained at 750°–1400° F., preferably 900° F.–1100° F., say 1100° F. (most preferably at about the same temperature as that employed in the first portion) in a flowing stream of hydrogen and and steam. This stream may contain 15–50 mole %, preferably 20–40 mole %, say 30 mole % of hydrogen, 50–85 mole %, preferably 60–80 mole %, say 70 mole % of steam, and 0–10 mole %, preferably 0–5 mole %, say about 0 mole % of inert gas such as helium, nitrogen, or light paraffins. Preferably the gas may consist essentially of hydrogen and steam in molar ratio of 0.2–1, typically 0.25–0.67, say 0.42:1.

When activation is carried out at atmospheric pressure, as in the preferred embodiment, the partial pressure of hydrogen may be 100–380, preferably 150–300, say 240 mm Hg; and the partial pressure of steam may be 380–660, preferably 460–610, say 520 mm Hg.

The second portion of the activation procedure may be carried out for 2–10 hours, preferably 2–5 hours, say 2 hours in a stream of flowing gas at a space velocity VHSV (STP) greater than about 1.5, preferably greater than 50, say 50–250, typically 150.

Post activation cooling is typically carried out by maintaining the activated catalyst in a stream of flowing steam for 1–10 hours, preferably 1–5 hours, say 2 hours as the temperature is lowered to the steam dealkylation temperature of 600° F.–950° F., preferably 650° F.–900° F., say 800° F. Preferably steam is present during post-activation in amount of 50–100 mole %, typically 80–100 mole %, say about 100 mole % of the flowing stream.

It is a feature of the process of this invention that steam dealkylation be carried out by passing charge steam and alkylaromatic hydrocarbon through a bed of steam dealkylating catalyst at steam dealkylating conditions for 30–150 seconds during a reaction period.

Steam dealkylation of the hydrocarbon charge may be carried out by passing the charge at 600° F.–950° F., preferably 650°–900° F., say 800° F. and pressure of 0–400 psig, preferably 0–200 psig, say 0 psig together with steam in amount of 2–25 moles, preferably 3–15 moles, say 6 moles per mole of hydrocarbon charge (corresponding to 100–125%, preferably 150%–750%, say 300% of the stoichiometric quantity) to a reaction zone. In commercial practice it may be desirable to operate at e.g. 125 psig to facilitate product recovery.

During steam dealkylation at these conditions, alkyl groups are removed from the charge alkylaromatic hydrocarbons to form product hydrocarbons bearing lesser numbers of alkyl groups on the aromatic nuclei. When the charge hydrocarbon contains ethylbenzenes for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain benzene.

During the reaction period of the short cycle operation, which occupies 30–180 seconds, preferably 30–120 seconds, say about 60 seconds, the activity of the steam dealkylation catalyst decreases. Typically this activity (as measured in terms of the mole percent conversion of charge alkylaromatic hydrocarbon) starts out at about 40%–100%, preferably 80%–100%, say 100%. As the reaction proceeds during the reaction period, the activity decreases so that at the end of the reaction period, it is only 20%–90%, preferably 50%–85%, say 75%.

When the activity has decreased to less than about 90% of the initial activity the reaction period is terminated or interrupted. Typically this occurs when the activity is 60%–85%, say 75% of the initial activity.

At the point when the reaction period is interrupted, the activity may be 20%–90%, preferably 50%–85%, say 75%.

Interruption or termination of the reaction period is effected by decreasing the flow (preferably to zero) of the charge alkylaromatic hydrocarbon.

The catalyst of decreased activity is preferably contacted with steam during a regeneration period of 90–540 seconds, preferably 90–450 seconds, say 180 seconds. The ratio of the regeneration time to the reaction time may be 1–5, preferably 2–4, say 3.

Regeneration of the catalyst of decreased activity may be effected by passing steam through the catalyst bed at 600° F.–950° F., preferably 650° F.–900° F., say 800° F. and pressure of 0–400 psig, preferably 0–200 psig, say 0 psig and at a WHSV of 0.1–10, preferably 0.2–2, say 0.3.

It is a feature of the process of this invention that regeneration may be carried out at substantially the same conditions as reaction; and in the preferred embodiment, the change from reaction to regeneration may be effected by decreasing, or preferably stopping, the flow of hydrocarbon—all other conditions preferably remaining substantially the same. The flow of charge hydrocarbon during regeneration may be 0%–50%, preferably 0%–10%, say 0% of the flow of charge hydrocarbon during the reaction period.

During regeneration, the activity of the catalyst may be increased to 30%–100%, preferably 72%–100%, say 100%. Typically the catalyst is regenerated to a level at which the activity is 75%–100%, preferably 90%–100%, say 100% of that prevailing at the beginning of the reaction period.

The so regenerated catalyst may be used in a subsequent reaction period—which may be followed by a subsequent regeneration period; etc. Reaction may be carried out for an indefinitely long time using the short cycling steam dealkylation process of this invention with alternating reaction and regeneration periods.

The product hydrocarbon exiting the process train may be condensed. The liquid condensate may represent a recovery of 50–94 mole %, preferably 70–94 mole %, say 85 mole % of the hydrocarbon charged.

In the case of a pure toluene charge for example, the product (moles per 100 moles of charge toluene) may contain the following:

TABLE

| Component | Broad | Preferred | Typical |
|---|---|---|---|
| Unreacted toluene | 4–79 | 13–70 | 37 |
| benzene | 20–61 | 30–60 | 55 |
| hydrogen | 60–183 | 90–180 | 165 |

TABLE-continued

| Component | Broad | Preferred | Typical |
|---|---|---|---|
| $CO_2$ | 20–61 | 30–60 | 55 |

The novel process of this invention permits attainment of more product per pound of catalyst than do typical prior processes. Commonly the amount of eg benzene product per pound of catalyst may be increased by a factor of 5–50 say 20 over and above that heretofore achieved.

DESCRIPTION OF PREFERRED EMBODIMENTS

Practice of the process of this invention will be apparent to those skilled in the art from the following illustrative embodiments wherein, as elsewhere in this description, all parts are parts by weight unless otherwise specifically stated.

EXAMPLES I–XII

An unsupported catalyst containing nickel oxide and chromium oxide (having the empirical formula 50 Ni:50 $Cr_2O_3$), in the form of cylindrical extrudates 0.125 inch diameter and 0.125 inch height are charged to a vertical fixed bed tubular reactor one inch in diameter and 18 inches long. The catalyst is centered in the reactor by 0.25 inch Berl saddles; and the reactor is operated in a downflow mode.

Steam is formed by pumping water to a preheater; and toluene is admitted to the steam line. The mixture passes through a second preheater prior to admission to the reactor. The upper portion of the reactor, packed with Berl saddles, serves as a preheater to bring the feed mixture to desired reaction temperature. The reactor is operated at atmospheric pressure. The reactor effluent is passed through a cold water condenser and then into a receiver in an ice-water bath. Liquid product is separated into two layers; and the hydrocarbon samples analyzed by gas chromatography using SE-30 columns. The off-gas volume is measured by wet test meter; and the off-gas samples are analyzed by mass spectroscopy.

The catalyst is activated by heating at a rate of 200° F. per hour to a maximum of 750° F. in the presence of flowing hydrogen at a WHSV of 600. The catalyst is then held at 750° F. for 2 hours in flowing hydrogen.

In the continuous flow operations of control Examples I–IV, steam and toluene are charged at constant rate and the run is considered started when hydrocarbon appears in the receiver. Each of Examples I–IV represents a five minute cut period taken between (I) 0–5, (II) 10–15, (III) 20–25, and (IV) 30–35 minutes after starting the run.

In experimental Examples V, VI, XI, and XII, the procedure includes a reaction period of 2.5 minutes during which steam and toluene are admitted to the reaction zone followed by a regeneration period of 3 minutes during which the toluene flow is stopped and the charge is steam alone. In experimental Examples VII–VIII, equal reaction and regeneration periods of 2 minutes were employed; in Examples IX and X, 3 minutes reaction, 2 minute regeneration cycles were employed.

The reaction conditions and results are as set forth in the following Table. It will be noted that Toluene Conversion and Benzene Yield are calculated on the basis of a 100% carbon balance which is essentially correct for all Examples except for Example V in which the carbon balance was only 36%.

The steam:toluene mole ratio and the toluene WHSV of Examples V–XII are calculated on the basis of the total cut period which includes both reaction and regeneration times. The toluene WHSV and the steam: toluene mole ratio during the reaction period of the total reaction—regeneration cycle are the same as those in the continuous flow operation.

TABLE

|  | I* | II* | III* | IV* | V | VI | VII | VIII | IX | X | XI | XII |
|---|---|---|---|---|---|---|---|---|---|---|---|---|
| Period Min. | 5 | 5 | 5 | 5 | 30 | 30 |  | 30 | 30 | 30 | 30 | 30 |
| Temp. °F. | 705 | 705 | 700 | 700 | 730 | 715 | 710 | 710 | 710 | 710 | 705 | 710 |
| Reaction:Regen (Min) | — | — | — | — | 2.5/3 | 2.5/3 | 2/2 | 2/2 | 3/2 | 3/2 | 2.5/3 | 2.5/3 |
| Toluene WHSV | 0.41 | 0.41 | 0.41 | 0.41 | 0.19 | 0.15 | 0.19 | 0.19 | 0.25 | 0.24 | 0.17 | 0.19 |
| Steam:Toluene Mole Ratio | 3.0 | 3.0 | 4.4 | 4.4 | 5.4 | 5.9 | 7.0 | 6.4 | 5.5 | 5.5 | 8.3 | 7.0 |
| Toluene Conv. Mole % Chg. | 60 | 55 | 53 | 42 | 80 | 72 | 74 | 79 | 69 | 64 | 69 | 71 |
| Benzene Yield Mole % Chg. | 42 | 41 | 40 | 30 | 40 | 44 | 39 | 38 | 37 | 35 | 34 | 34 |

*Control

From the above table it is apparent that during the continuous flow operation of Examples I–IV, the catalyst deactivates rapidly. After four cut periods of 5 minutes each (over a total period of 35 minutes run), the conversion drops from 60% down to 42%. In contrast, in Examples V–XII, the toluene conversion over 240 minutes is never below 64%. It is also apparent that the benzene yield in control Examples I–IV drops from 42% to 30% after only a period of 35 minutes. In experimental Examples V–XII, the benzene yield is above the 30% level over the entire period of 240 minutes.

EXAMPLES XIII–XVI

In this series of examples the support used was American Cyanamid Aero 100 Brand, one-sixteenth inch, extrudates of gamma alumina.

Prior to use, the alumina is charged into a stainless steel tubular reaction and heated to 1110° F. for 12 hours while passing steam (WHSV of 0.064) and air (VHSV of 226) through the bed. The steamed alumina is then calcined for two hours at 1000° F. The surface area of the alumina is reduced by this treatment from an initial value of 231 $m^2/g$ to a final value of 192 $m^2/g$.

166 parts of steam sintered alumina support is placed within a container and chilled in an ice bath. 257 parts of aqueous solution containing 148.5 parts of nickelous nitrate hexahydrate $Ni(NO_3)_2.6H_2O$ and 8.6 parts of potassium nitrate $KNO_3$ are poured over the chilled support. The resulting material is dried by heating overnight at 200° F. and then by heating for two hours at 300° F. The metal salts are decomposed by heating in air at 700° F. for Ca 6 hours; and the catalyst is calcined in a muffle furnace at 700° F. for two hours. The so-prepared experimental catalyst contains 15.5% NiO (12.5% Ni), 1.8% $K_2O$, and 74.1% $Al_2O_3$.

The catalyst is charged into a fixed bed tubular reactor (one inch i.d. and 18 inches long)—it is centered in the reactor by 0.25 inch Berl saddles. The reactor is operated in a vertical downflow mode. Steam is formed by passing water to a preheater; and toluene is admitted to the steam line. The mixture is passed through a second preheater before entering the reactor.

The upper part of the reactor, which is packed with Berl saddles also serves as a preheater to bring the feed mixture to desired reaction temperature. Reactor operation is at atmospheric pressure; and the effluent is passed through a cold water condenser and then into a receiver which is cooled to ice-water temperature.

The liquid condensate is separated into two layers and the hydrocarbon samples analyzed by gas chromatography. The off-gas is measured in a wet test meter and analyzed by mass spectroscopy.

In the course of operation, the catalyst is activated by contact with following hydrogen (VHSV of 432) as heating is continued at a rate of 200° F./hr to a final temperature of 900° F., followed by holding at 900° F. for 14 hours in the presence of flowing (VHSV of 216) hydrogen, followed by holding at 900° F. in the presence of steam (water WHSV of 0.36) and hydrogen (VHSV of 216) for 2 hours. Hydrogen flow is then stopped and the catalyst is brought to reactant temperature in the presence of steam.

In operation, a mixture of steam and toluene is charged at constant rate; and the run is considered started when hydrocarbon appears in the receiver. The run is carried out using short cycling i.e. a period of 2.5 minutes of reaction charging toluene plus steam is followed by a period of 3 minutes of regeneration charging steam alone.

In this series of examples, each example was carried out over 45 minutes at selected temperatures; and the following were measured:

(a) temperature in °F.—average temperature in the bed;

(b) WHSV—hourly space velocity of toluene charge;

(c) Steam: toluene mol ratio—this, like the WHSV, being calculated on the basis of the total cut period of 45 minutes and includes both reaction and regeneration times;

(d) Carbon Balance—% of charge;

(e) Toluene conversion—mole % of the charge converted to products—based upon 100% carbon balance;

(f) Benzene yield—mole % of the charge converted to benzene—based upon 100% carbon balance;

(g) Benzene selectivity—mole % of benzene in the converted products.

TABLE

|  | EXAMPLE | | | |
|---|---|---|---|---|
|  | XIII | XIV | XV | XVI |
| Temp. °F. | 660 | 730 | 800 | 875 |
| Toluene WHSV | 0.32 | 0.27 | 0.27 | 0.29 |
| St:Tol mole ratio | 9.7 | 10.1 | 10.4 | 9.8 |
| Carbon Balance % charge | 93 | 104 | 110 | 101 |
| Tol. Conv. Mol. % Chge | 39 | 54 | 76 | 84 |
| Benzene Yield Mcl. % Chge | 36 | 48 | 61 | 55 |
| Benzene Sel Mol. % | 93 | 89 | 80 | 65 |

From the above table it is apparent that the novel process of this invention permits steam dealkylation of toluene to give benzene product in high conversion, yield, and selectivity. In the preferred embodiment, operating at 800° F. for example, it is possible to attain a conversion of 76%, a selectivity of 80%, and a yield of 61%.

In prior techniques at comparable temperatures, the selectivity and yield may be only about 24%–25% i.e. the number of moles of benzene produced per mole of charge toluene may be less than half that obtained when following the process of the instant invention.

EXAMPLES XVII–XXIX

In this series of control examples the same catalyst was used as for Examples XIII–XVI. It was activated by contact with flowing hydrogen (VHSV of 432) as it is heated at a rate of 200° F./hr to a final temperature of 900° F., followed by holding at 900° F. for 14 hours (with a flow of hydrogen at VHSV of 216)—followed by an additional 2 hours in the presence of flowing steam (water VHSV of 0.36) and hydrogen (VHSV of 216). At the end of activation, the hydrogen flow is stopped; and the reactor is brought to the desired temperature of 800° F. (Example XVII is run at 785° F.).

In each Example, the product is collected for a fixed period—Example XVII—5 minutes, Example XVIII—15 minutes, Example XIX—40 minutes, Examples XXI to XXIX—60 minutes.

At the end of Example XXIV, the reactor is flushed with hydrogen and left under hydrogen (75–90 psig) at 800° F. for about 16 hours.

TABLE

| Example | Toluene WHSV | St:Tol Mol Ratio | Tol. Conv. Mol % Chg | Benz. Yield Mol % Chg |
|---------|--------------|------------------|----------------------|------------------------|
| XVII    | 1.19         | 1.5              | 72                   | 51                     |
| XVIII   | 1.31         | 2.6              | 60                   | 59                     |
| XIX     | 1.29         | 2.4              | 51                   | 47                     |
| XX      | 1.29         | 2.5              | 30                   | 28                     |
| XXI     | 1.30         | 2.0              | 31                   | 29                     |
| XXII    | 1.29         | 2.0              | 30                   | 27                     |
| XXIII   | 1.29         | 2.0              | 30                   | 21                     |
| XXIV    | 1.29         | 2.1              | 29                   | 27                     |
| XXV     | 1.29         | 2.1              | 42                   | 37                     |
| XXVI    | 1.28         | 2.0              | 38                   | 35                     |
| XXVII   | 0.45         | 5.7              | 41                   | 37                     |
| XXVIII  | 1.28         | 2.1              | 36                   | 33                     |
| XXIX    | 1.28         | 2.0              | 33                   | 28                     |

From the above Table, it is apparent that use of a (nominal) 15 NiO-2K$_2$O-83 Al$_2$O$_3$ catalyst during continuous flow operation permits initial conversion of 72 mol % of the toluene to give a benzene yield of 51 mol %. During continuous flow operation, the catalyst activity decreases to give a toluene conversion of 51% after one hour and of 29%–31% after 6 hours. Standing overnight in hydrogen (Ex XXV) temporarily regenerates the catalyst; but after 4 hours the catalyst activity declines to give a benzene yield of—28 mol %.

EXAMPLES XXX–XXXV

In this series of Examples, the same system was used as for Examples XVII–XXIX. The cut period for each example is 60 minutes and the temperature is 800° F. Each example is run on a short cycle basis in which reaction occurs for one minute during which toluene and steam are passed through the bed followed by regeneration for three minutes during which only steam is passed through the bed.

At the end of Example XXX, the reactor was flushed with hydrogen and left under hydrogen at 75–90 psig at 800° F. for 16 hours.

The steam to toluene ratio is calculated on a basis of total cut period which includes regeneration and reaction times.

As used in Example XXX, the catalyst is deactivated i.e. not treated further but used as recovered from Example XXIX.

TABLE

| Example | Toluene WHSV | St:Tol Mol. Ratio | Tol. Conv. Mol % Chg | Benz. Yield Mol % Chg |
|---------|--------------|-------------------|----------------------|------------------------|
| XXX     | 0.20         | 12.8              | 46                   | 40                     |
| XXXI    | 0.19         | 14.0              | 73                   | 60                     |
| XXXII   | 0.21         | 11.8              | 70                   | 55                     |
| XXXIII  | 0.15         | 16.8              | 70                   | 58                     |
| XXXIV   | 0.21         | 11.8              | 69                   | 55                     |
| XXXV    | 0.29         | 8.6               | 60                   | 52                     |

Comparison of the data developed during continuous flow in Examples XVI–XXIX and that developed during short cycle operation in accordance with practice of the process of this invention reveals the advantages of the latter. During the continuous flow operation, the catalyst activity (in terms of Toluene Conversion) decreases within one hour from 72% to 51%. It then decreases further over six hours to a low level of 29%–31%. Although the catalyst may be temporarily regenerated by standing overnight in hydrogen, the activity quickly drops.

Practice of the novel process of this invention for only one hour increases the Toluene Conversion from 33% (Ex XXIX) to 46% (Ex XXX). This is unexpected. Furthermore, the catalyst retains its activity for four hours (i.e. during Example XXXI–XXXIV) at levels to give a Toluene Conversion of 69%–73% which level is only achieved in the control examples (Example XVII) for the first few minutes of reaction. This clearly demonstrates the unexpected and unobvious improvements which may be achieved—not only is it possible to attain the unusually high yield and conversion, it is also possible to utilize this process to regenerate a deactivated catalyst.

EXAMPLES XXXVI–XXXVII

In this pair of comparative examples, the catalyst is prepared by impregnating powdered silica-stabilized alumina (Harshaw Al-1605P) with a solution containing ammonium dichromate. After drying, a solution containing half the required nickel nitrate was added to the powder. After drying and decomposing to decompose the dichromate, the powder was treated with a solution containing potassium nitrate and the balance of the nickel nitrate. The catalyst was extruded through a one-eighth inch die and calcined.

Analysis of the finished catalyst was: 13.9 W% Ni, 14.0 W% Cr$_2$O$_3$; 1.7 W% K$_2$O; and 55.9 W% Al$_2$O$_3$. The catalyst was activated in the reactor at 1100° F. over night in a stream of hydrogen before use.

For each run, there is noted infra for each one hour period: the recovery i.e. the liquid hydrocarbon recovery as weight percent of the reformate charge; the balance i.e. the overall all material balance in terms of the weight percent of the charge recovered as product; the Conversion i.e. the mole % of the C$_9$ to C$_{11}$ charge which has been converted; and the BTX yield i.e. the amount of BTX recovered expressed as mole % of the C$_9$ to C$_{11}$ charge.

These catalysts were used to process a heavy reformate (depentanizer bottoms) having the following GC analysis:

| Component | Wt. % |
|---|---|
| Light Material | 6.8 |
| Benzene (B) | 0.5 |
| Toluene (T) | 2.3 |
| Xylene & Ethylbenzene (X) | 33.9 |
| C$_9$ to C$_{11}$ Aromatics | 56.6 |

In control Example XXXVI*, the reaction was carried out at continuous flow conditions. Charge space velocity (WHSV) of reformate was 1.3 and of steam was 1.2. 6.3 moles of steam were charged per mole of reformate. Temperature of operation was 870° F.–875° F. Data was taken by collecting (and analyzing) samples over six one-hour periods.

In experimental Example XXXVII, the cycle was 1 minute processing (stream plus reformate) followed by 3 minutes regeneration (steam alone). Space velocity (WHSV) of reformate was 0.4 g reformate per gram of catalyst per hour total time; steam WHSV was 1.2. 5.5 moles of steam were charged per mole of reformate. Temperature was 870° F.–875° F.

| EXAMPLE XXXVI* | | | | | | |
|---|---|---|---|---|---|---|
| Period | 1 | 2 | 3 | 4 | 5 | 6 |
| Recovery | 53 | 66 | 68 | 70 | 70 | 74 |
| Balance | 97 | 100 | 100 | 100 | 98 | 100 |
| Conversion | 89 | 86 | 82 | 78 | 81 | 75 |
| BTX Yield | 32 | 56 | 55 | 54 | 53 | 57 |

| EXAMPLE XXXVII | | | | | | |
|---|---|---|---|---|---|---|
| Period** | 1 | 2 | 3 | 4 | 5 | 6 |
| Recovery | 53 | 55 | | 53 | 66 | 56 |
| Balance | 99 | 98 | | 97 | 99 | 96 |
| Conversion | 94 | 94 | | 94 | 92 | 93 |
| BTX Yield | 44 | 48 | | 42 | 69 | 47 |

*Sample not recovered during third period.

From these two examples, its clear that the process of this invention (Example XXXVII) gives a Conversion which averages out (and in fact is essentially constant) at about 94%. In contrast, in the control run the conversion steadily drops by 14% during the six hours of operation and the average is about 82%—which is 12% less than is obtained by the process of the invention.

Although this invention has been illustrated by reference to specific embodiments, it will be apparent to those skilled in the art that various changes and modifications may be made which clearly fall within the scope of this invention.

We claim:

1. The method of steam dealkylating a charge alkylaromatic hydrocarbon which comprises
    passing a mixture consisting essentially of steam and charge alkylaromatic hydrocarbon into contact with a steam dealkylation catalyst at steam dealkylating reaction conditions for 30–180 seconds during which time the activity of the steam dealkylation catalyst, as measured by the mole percent conversion of charge alkylaromatic hydrocarbon to product dealkylated alkylaromatic hydrocarbon, decreases during the reaction period;
    interrupting the flow of charge alkylaromatic hydrocarbon, thereby interrupting said reaction period, when the activity of said catalyst has decreased;
    thereafter contacting said catalyst of decreased activity with steam during a regeneration period at regenerating conditions for 90–540 seconds, as the activity of said catalyst increases, thereby forming regenerated catalyst; and
    recovering product dealkylated alkylaromatic hydrocarbon.

2. The method of steam dealkylating a charge alkylaromatic hydrocarbon as claimed in claim 1 wherein the ratio of regeneration time to reaction time is about 1–5:1.

3. The method of steam dealkylating a charge alkylaromatic hydrocarbon as claimed in claim 1 wherein the ratio of regeneration time to reaction time is about 3:1.

4. The method of steam dealkylating a charge alkylaromatic hydrocarbon as claimed in claim 1 wherein the regeneration time is about 180 seconds and the reaction time is about 60 seconds.

5. The method of steam dealkylating a charge alkylaromatic hydrocarbon as claimed in claim 1 wherein said charge alkylaromatic hydrocarbon contains toluene.

6. The method of steam dealkylating a charge alkylaromatic hydrocarbon as claimed in claim 1 wherein said charge alkylaromatic hydrocarbon contains a C$_9$–C$_{11}$ hydrocarbon fraction.

7. The method of steam dealkylating a charge alkylaromatic hydrocarbon which comprises
    passing a mixture consisting essentially of steam and charge alkylaromatic hydrocarbon into contact with a steam dealkylation catalyst at steam dealkylating reaction conditions for 30–180 seconds during which time the activity of the steam dealkylation catalyst, as measured by the mole percent conversion of charge alkylaromatic hydrocarbon to product dealkylated alkylaromatic hydrocarbon, decreases to less than about 90% of the initial activity during a reaction period;
    interrupting the flow of said charge alkylaromatic hydrocarbon, thereby interrupting said reaction period when the activity of said catalyst has decreased to less than about 90%;
    thereafter contacting said catalyst of decreased activity with steam during a regeneration period at regenerating conditions for 90–540 seconds, as the activity of said catalyst increases to at least about 75% of the initial activity thereby forming regenerated catalyst; and
    recovering product dealkylated alkylaromatic hydrocarbon.

8. The method of steam dealkylating a charge alkylaromatic hydrocarbon as claimed in claim 7 wherein the reaction period is interrupted when the activity of the catalyst is decreased to about 20%–90% of its initial activity.

9. The method of steam dealkylating a charge alkylaromatic hydrocarbon as claimed in claim 7 wherein the reaction period is interrupted when the activity of the catalyst has decreased to about 60%–85% of its initial activity.

10. The method of steam dealkylating a charge alkylaromatic hydrocarbon as claimed in claim 7 wherein the catalyst is regenerated during the regeneration period to an activity of 75%–100% of the initial activity.

11. The method of steam dealkylating a charge alkylaromatic hydrocarbon as claimed in claim 7 wherein said steam dealkylating reaction conditions and said regenerating conditions include temperature of 600° F.-950° F. and pressure of 0-400 psig.

12. The method of steam dealkylating a charge alkylaromatic hydrocarbon as claimed in claim 7 wherein the temperature and pressure are substantially the same during said reaction and said regeneration.

13. The method of steam dealkylating a charge alkylaromatic hydrocarbon as claimed in claim 7 wherein the flow of alkylaromatic hydrocarbon during said regeneration period is substantially interrupted during said regeneration period.

14. The method of steam dealkylating a charge alkylaromatic hydrocarbon as claimed in claim 7 wherein the flow of alkylaromatic hydrocarbon during said regeneration period is 0%-50% of the flow of said hydrocarbon during said reaction period.

15. The method of steam demethylating charge toluene which comprises passing a mixture consisting essentially of steam and toluene into contact with a steam demethylating catalyst at steam demethylating conditions including temperature of 600° F.-950° F. for 30-180 seconds during which time the activity of the steam demethylation catalyst, as measured by the mole percent conversion of charge toluene to product benzene, decreases during a reaction period;

interrupting the flow of toluene, thereby interrupting said reaction period when the activity of said catalyst has decreased;

thereafter contacting said catalyst of decreased activity with steam during a regeneration period at regenerating conditions including temperature of 600° F.-950° F., as the activity of said catalyst increases thereby forming regenerated catalyst; and recovering product benzene.

16. The method of steam demethylating charge toluene as claimed in claim 15 which comprises passing a mixture consisting essentially of steam and toluene into contact with a steam demethylation catalyst at steam demethylating conditions including temperature of 600° F.-950° F. for 30-180 seconds during which time the activity of the steam demethylation catalyst, as measured by the mole percent conversion of charge toluene to product benzene has decreased to less than about 90% of the initial activity during a reaction period;

interrupting the flow of toluene, thereby interrupting said reaction period when the activity of said catalyst has decreased to less than about 90%;

thereafter contacting said catalyst of decreased activity with steam during a regeneration period at regenerating conditions including temperature of 600° F.-900° F., as the activity of said catalyst increased to at least about 75% of its initial activity thereby forming regenerated catalyst; and recovering product benzene.

17. The method of steam demethylating charge toluene which comprises passing a mixture consisting essentially of steam and toluene into contact with a steam demethylation catalyst at steam demethylating conditions including temperatures of 650° F.-900° F., pressure of 0-200 psig, and steam to hydrocarbon mole ratio of 2-25:1 for 30-180 seconds during which time the activity of the steam demethylating catalyst, as measured by the mole percent conversion of charge toluene to product benzene decreases to 50-90% of its initial activity during a reaction period;

interrupting the flow of toluene, thereby interrupting said reaction period when the activity of said catalyst has decreased to a point at which the activity is less than 90% of the initial activity;

decreasing the flow of toluene to 0%-50% of that of the reaction period during a regenerating period;

therewith contacting said catalyst of decreased activity with steam at regenerating conditions including temperature of 650° F.-900° F., pressure of 0-400 psig, and a weight hourly space velocity WHSV of 0.1-10 for 90-540 seconds as the activity of said catalyst increases to 80%-100% of its initial activity thereby forming regenerated catalyst; and recovering product benzene.

18. The method of steam dealkylating charge alkylaromatic hydrocarbon containing $C_9$-$C_{11}$ hydrocarbon components which comprises passing a mixture consisting essentially of steam and charge into contact with a steam dealkylation catalyst at steam dealkylating conditions including temperature of 600° F.-950° F. for 30-180 seconds during which time the activity of the steam dealkylation catalyst, as measured by the mole percent conversion of charge alkylaromatic to product dealkylate decreases to less than about 90% of the initial activity during a reaction period;

interrupting the flow of charge alkylaromatic hydrocarbon thereby interrupting said reaction period when the activity of said catalyst has decreased to less than about 90%;

thereafter contacting said catalyst of decreased activity with steam during a regeneration period at regenerating conditions including temperature of 600° F.-900° F., as the activity of said catalyst increases to at least about 75% of its initial activity thereby forming regenerated catalyst; and recovering product dealkylate.

19. The method of activating an unactivated steam dealkylation catalyst $$a(VIII)2/n0:b(VI)2/m0:c(I)20:d(Supp)$$

wherein a is 0.002-0.75; VIII represents a metal having valence n of Group VIII of the Periodic Table; b is 0-0.78; c is 0.00003-0.17; VI represents a metal having valence m, of Group VIB of the Periodic Table; I represents a metal of Group I of the Periodic Table; d is 0.15-0.95; and Supp represents the catalyst support which comprises (a) maintaining the unactivated catalyst in a hydrogen atmosphere at 950° F.-1400° F. for 2-10 hours thereby forming a hydrogen-treated catalyst;

(b) maintaining the hydrogen-treated catalyst in a steam-hydrogen atmosphere at 950° F.-1400° F. for 2-10 hours thereby forming a steamed hydrogen-treated catalyst;

(c) preferably cooling the steamed hydrogen-treated catalyst to 650° F.-900° F. in a steam or steam-hydrogen atmosphere thereby forming an activated catalyst; and (d) recovering said activated catalyst.

* * * * *